(12) United States Patent
Mukaiyama et al.

(10) Patent No.: US 7,256,215 B2
(45) Date of Patent: Aug. 14, 2007

(54) CRYSTALS OF 5-HYDROXYCARBAMIMIDOYL-2-HYDROXYBENZENESULFONAMIDE DERIVATIVE

(75) Inventors: Harunobu Mukaiyama, Nagano (JP); Yuichiro Kai, Nagano (JP); Hideki Takeuchi, Nagano (JP); Kenji Yokoyama, Nagano (JP); Yoshihiro Terao, Nagano (JP); Satoshi Akahane, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 374 days.

(21) Appl. No.: 10/507,616

(22) PCT Filed: Mar. 4, 2003

(86) PCT No.: PCT/JP03/02465

§ 371 (c)(1),
(2), (4) Date: Sep. 14, 2004

(87) PCT Pub. No.: WO03/078389

PCT Pub. Date: Sep. 25, 2003

(65) Prior Publication Data

US 2005/0143457 A1 Jun. 30, 2005

(30) Foreign Application Priority Data

Mar. 15, 2002 (JP) .............................. 2002-071120

(51) Int. Cl.
*C07C 307/00* (2006.01)
*A61K 31/235* (2006.01)
(52) U.S. Cl. ........................................ 514/532; 560/13
(58) Field of Classification Search .................. 560/13; 514/532
See application file for complete search history.

(56) References Cited

U.S. PATENT DOCUMENTS

2006/0116361 A1* 6/2006 Okazaki et al. ............. 514/183
2006/0205812 A1* 9/2006 Okazaki et al. ............. 514/534

FOREIGN PATENT DOCUMENTS

| WO | WO 00/78747 A1 | 12/2000 |
| WO | WO 01/30756 A1 | 5/2001 |
| WO | WO 02/28827 A1 | 4/2002 |
| WO | WO 03/078389 A1 | 9/2003 |

\* cited by examiner

*Primary Examiner*—Taylor Victor Oh
(74) *Attorney, Agent, or Firm*—Sughrue Mion, PLLC

(57) ABSTRACT

The present invention provides a novel crystalline form of n-butyl[4-[2-[2-hydroxy-5-(N-hydroxycarbamimidoyl) benzenesulfonylamino]ethyl]-2'-methanesulfonyl-3-yloxy] acetate hydrochloride, pharmaceutical compositions containing the same and their uses, which exhibits excellent inhibitory activities against activated blood coagulation factor X, and is useful for the treatment or prevention of a tromboembolic disease.

2 Claims, 3 Drawing Sheets

CRYSTALS OF 5-HYDROXYCARBAMIMIDOYL-2-HYDROXYBENZENESULFONAMIDE DERIVATIVE

TECHNICAL FIELD

The present invention relates to a novel crystal of n-butyl [4-[2-[2-hydroxy-5-(N-hydroxycarbamimidoyl)benzenesulfonyl amino]ethyl]-2'-methanesulfonylbiphenyl-3-yloxy] acetate hydrochloride, and their uses.

BACKGROUND ART n-Butyl[4-[2-[2-hydroxy-5-(N-hydroxycarbamimidoyl) benzenesulfontylamino]ethyl]-2'-methanesulfonylbiphenyl-3-yl oxy]acetate hydrochloride represented by formula (I):

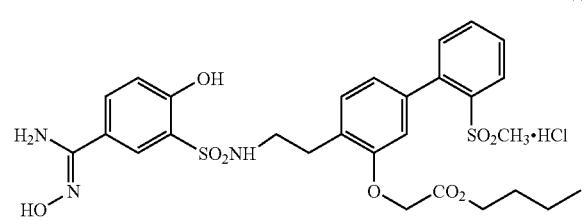

is a novel compound which has been found by the present applicant. This compound exhibits excellent inhibitory activities against activated blood coagulation factor X, and is useful for the treatment or prevention of a thromboembolic disease. Crystalline polymorphism of this compound has not been found so far.

DISCLOSURE OF THE INVENTION

Crystals of compound (I) (hereinafter referred to as "crystalline form A") prepared by the methods disclosed in the examples of Japanese application 2000-305569, have unsatisfactory stabilities, and when stored for a long period, it has serious problems to decrease the content of the active ingredient. Moreover, crystalline form A has undesirable handing properties of having a low filtration rate for a large scale production, and is not suitable for a commercial production. The present inventors had intensively investigated crystals of n-butyl[4-[2-[2-hydroxy-5-(N-hydroxycarbamimidoyl)benzene sulfonylamino]ethyl]-2'-methanesulfonylbiphenyl-3-yloxy]acetate hydrochloride which have good stabilities and are suitable for a commercial production, and found that compound (I) has two crystalline forms of "crystalline form B" and "a crystalline monohydrate of compound (I)" other than crystalline form A. Among them, a crystalline monohydrate of compound (I) is difficult to prepare pharmaceutical formulations due to its poor water solubility. On the contrary, the present inventors have discovered unexpectedly that crystalline form B is highly water-soluble and has a good oral bioavailability. Furthermore, crystalline form B has good storage stabilities and a high filtration rate, and is suitable for a commercial production. Based on these findings, the present invention has been accomplished.

The present invention therefore provides:

(1) a crystal of n-butyl[4-[2-[2-hydroxy-5-(N-hydroxycarbamimidoyl)benzenesulfonylamino]ethyl]-2'-methanesulfonylbiphenyl-3-yl oxy]acetate hydrochloride, which shows an X-ray powder diffraction pattern (hereinafter referred to as "crystalline form B") having characteristic peaks at a diffraction angle (2θ±0.1 degree) of 5.4, 8.6, 9.1, 12.1, 16.7, 17.3 and 21.0 degrees;

(2) a pharmaceutical composition which comprises, as an active ingredient, a crystal according to the above (1);

(3) the pharmaceutical composition according to the above (2), for the treatment or prevention of a thromboembolic disease;

(4) a use of a crystal according to the above (1), for the manufacture of a medicament for treating or preventing a thromboembolic disease;

(5) a method for treating a thromboembolic disease, which comprises administering a therapeutically effective amount of a crystal according to the above (1).

BEST MODE FOR CARRYING OUT THE INVENTION

Crystalline form B of the present invention can be prepared as follows.

An arbitrary crystalline form of a compound represented by formula (I) is dissolved with butanol under heating, the amount of which is in the range of about 4 to about 10 parts by weight, preferably about 4 to about 7 parts by weight on the basis of 1 part by weight of compound (I). Thereafter, if required, to the resulting solution is added a poor solvent in which compound (I) is poorly soluble, at a temperature of about 20° C. to about 50° C., and the mixture is stood or stirred at a temperature of about 0° C. to about 30° C. for about 3 to about 24 hours to provide crystalline form B of the present invention. Examples of poor solvents include ethyl acetate, acetone, methyl ethyl ketone, diethylether, tert-butyl methyl ether, 1,2-dimethoxyethane, tetrahydrofuran, toluene, xylene, chlorobenzene, acetonitrile and the like, which can be used singly or as a mixture of one or more solvents. The amount of poor solvents is varied depending on the type of poor solvents, and is ordinarily in the range of about 0.5 to about 2 parts by weight on the basis of a part by weight of butanol.

Figure 1:
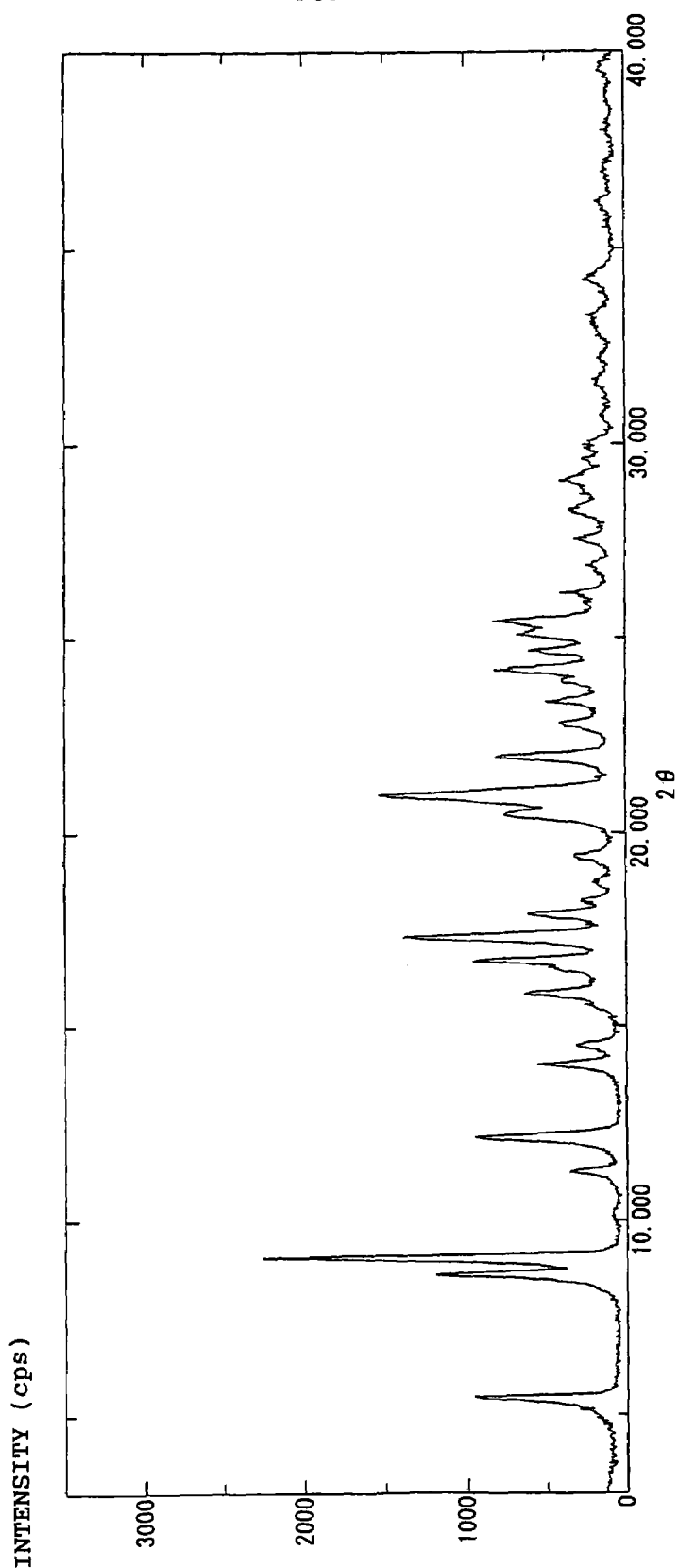
FIG. 1 is an X-ray powder diffraction pattern of crystalline form B of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride obtained in Example 1 where, the ordinate shows the X-ray intensity in cps and the abscissa shows the diffraction angle in 2θ.

Crystalline form B thus obtained can be identified by their characteristic diffraction peaks at a diffraction angle (2θ±0.1 degree) of 5.4, 8.6, 9.1, 12.1, 16.7, 17.3 and 21.0 degrees) as shown in the X-ray powder diffraction charts of FIG. 1.

Crystalline form B of the present invention can be stored under ordinarily storage conditions such as 25° C./60% relative humidity and the like for a long period without changing its crystalline form, and formulated into powders, granules, tablets, capsules, injections or the like according to conventional methods.

In the case of using a pharmaceutical composition comprising a crystal of the present invention as an active ingredient, various dosage forms can be administered depending upon their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical additives such as excipients, disintegrators, binders, lubricants, diluents, buffers, isotonic agents, preservatives, wetting agents, emulsifying agents, dispersing agents, stabilizing agents, solubilizing agents and the like, according to conventional formulation procedures depending upon their dosage forms.

In the case of using a pharmaceutical composition for a medical treatment, the dosage of a crystal of the present invention as an active ingredient is appropriately determined depending on the age, sex or body weight of the individual patient, the severity of the disease, the condition to be treated and the like. A typical dosage for oral administration is in the range of from about 1 mg to about 5000 mg per day per adult human. A typical dosage for parenteral administration is in the range of from about 0.01 mg to about 500 mg per day per adult human. The dosages may be administered in single or divided doses, for example one to several times daily.

EXAMPLE

The following examples, reference examples and test examples illustrate the invention in further detail. It is to be understood, however, that they are not to be construed as limiting the scope of the invention in any way.

X-ray powder diffraction patterns of each crystalline form were obtained using an X-ray diffraction analyzer, RINT2100 (Rigaku) which was operated at 40 kV/40 mA and using CuKα-ray beam. Melting points of each crystalline form were determined using a thermogravimetry/differential thermal analyzer (TG/DTA, Rigaku: Thermo plus TG8120) which was measured at a heating rate of 10° C./min. Melting points of each crystalline form were shown as an extrapolated onset temperature.

Reference Example 1

Crystalline form A of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride (Step 1)

7-Hydroxycroman-2-one

A mixture of 100 g of 7-hydroxycromen-2-one, 10 g of 10% palladium on carbon, 500 mL of tetrahydrofuran and 800 mL of ethanol was stirred under a hydrogen atmosphere at 65° C. for 15 hours. To the reaction mixture was added a suspension of 10 g of 10% palladium on carbon in 200 mL of ethanol under ice-cooling, and the mixture was stirred under a hydrogen atmosphere at 65° C. for 15 hours. The reaction mixture was filtered through a diatomaceous earth, and the filtrate was concentrated under reduced pressure to give 106.5 g of colorless 7-hydroxycroman-2-one.

$^1$H-NMR (CDCl$_3$) δ ppm: 2.75-2.96 (4H, m), 5.81 (1H, br s), 6.59-6.66 (2H, m), 7.04 (1H, d, J=7.9 Hz)

(Step 2)

7-Benzyloxycroman-2-one

To a stirred suspension of 202.4 g of 7-hydroxycroman-2-one and 341.0 g of potassium carbonate in N,N-dimethylformamide was added 153.2 mL of benzyl chloride at room temperature, and the mixture was stirred at room temperature for 15 hours. After the reaction mixture was concentrated under reduced pressure to remove the solvent, the residue was added to a mixture of ethyl acetate and water. The organic layer was separated, washed with water, dried over anhydrous sodium sulfate, and filtered. The filtrate was concentrated under reduced pressure, and the residue was triturated in diisopropyl ether-hexane. The solid was collected by filtration to give 266.1 g of 7-benzyloxycroman-2-one as a pale brown solid.

$^1$H-NMR (CDCl$_3$) δ ppm: 2.73-2.81 (2H, m), 2.90-2.98 (2H, m), 5.05 (2H, s), 6.68 (1H, d, J=2.5 Hz), 6.73 (1H, dd, J=8.3, 2.5 Hz), 7.08 (1H, d, J=8.3 Hz), 7.30-7.46 (5H, m)

(Step 3)

3-(4-Benzyloxy-2-hydroxyphenyl)propionamide

To a solution of 33.26 g of 7-benzyloxycroman-2-one in 264 mL of tetrahydrofuran was added 82 mL of 28% aqueous ammonia solution at room temperature. After the mixture was stirred at room temperature for 20 minutes, to the reaction mixture was added 654 mL of 1 mol/L hydrochloric acid in an ice-bath. The resulting suspension was diluted with about 1 L of water, and the precipitate was collected by filtration to give 34.8 g of 3-(4-benzyloxy-2-hydroxyphenyl)propionamide as a colorless powder.

$^1$H-NMR (CDCl$_3$) δ ppm: 2.60-2.70 (2H, m), 2.80-2.90 (2H, m), 5.01 (2H, s), 5.46 (2H, br s), 6.49 (1H, dd, J=8.5, 2.5 Hz), 6.58 (1H, d, J=2.5 Hz), 6.93 (1H, d, J=8.5 Hz), 7.28-7.45 (5H, m), 8.67 (1H, s)

(Step 4)

3-(4-Benzyloxy-2-methoxymethoxyphenyl)propionamide

To a stirred suspension of 5.64 g of 60% sodium hydride in oil in 628 mL of N,N-dimethylformamide was added 34.8 g of 3-(4-benzyloxy-2-hydroxyphenyl)propionamide under ice-cooling, and the mixture was stirred at 50° C. for 40 minutes. To the reaction mixture was added 12.39 g of chloromethyl methyl ether under ice-cooling, and the mixture was stirred at room temperature for 15 hours. After the reaction mixture was concentrated under reduced pressure to remove the solvent, the residue was poured into a mixture of 500 mL of ethyl acetate, 100 mL of toluene and 200 mL of water. The organic layer was separated, washed with water, dried over anhydrous magnesium sulfate, and filtered. The filtrate was concentrated under reduced pressure to give a colorless solid. The solid was triturated in ethyl acetate-diisopropyl ether and collected by filtration to give 35.3 g of 3-(4-benzyloxy-2-methoxy-methoxyphenyl)propionamide as a colorless solid.

¹H-NMR (CDCl₃) δ ppm: 2.50 (2H, t, J=7.6 Hz), 2.91 (2H, t, J=7.6 Hz), 3.47 (3H, s), 5.02 (2H, s), 5.18 (2H, s), 5.25-5.45 (2H, m), 6.56 (1H, dd, J=8.5, 2.5 Hz), 6.77 (1H, d, J=2.5 Hz), 7.07 (1H, d, J=8.5 Hz), 7.30-7.45 (5H, m)

(Step 5)

2-(4-Benzyloxy-2-methoxymethoxyphenyl)ethylamine

To a solution of 28.42 g of 3-(4-benzyloxy-2-methoxymethoxyphenyl)propionamide and 40.4 mL of 1,8-diazabicyclo-[5.4.0]-7-undecene in 895 mL of methanol was added 16.04 g of N-bromosuccinimide at 65° C. After the mixture was stirred at 65° C. for 15 minutes, to the reaction mixture was added additional 16.04 g of N-bromosuccinimide at 65° C. After being stirred at 65° C. for 15 minutes, the resultant mixture was concentrated under reduced pressure to remove the solvent. To the residue were added water and ethyl acetate, and the organic layer was separated. The organic layer was washed with water, dried over anhydrous magnesium sulfate, and filtered. The filtrate was concentrated under reduced pressure to give an oily product. To a solution of this residue in 242 mL of ethanol was added 67.6 mL of 8 mol/L aqueous potassium hydroxide solution, and the mixture was refluxed for 15 hours. The reaction mixture was concentrated under reduced pressure to remove the solvent. To the residue were added 500 mL of ethyl acetate, 50 mL of toluene and 300 mL of water, and the organic layer was separated. The organic layer was washed with water, dried over anhydrous magnesium sulfate, and filtered. The filtrate was concentrated under reduced pressure, and the residue was purified by medium pressure liquid column chromatography on silica gel (eluent: hexane-ethyl acetate) to give 80.0 g of 2-(4-benzyloxy-2-methoxymethoxy phenyl)ethylamine as a colorless oil.

¹H-NMR (CDCl₃) δ ppm: 1.31 (2H, br s), 2.71 (2H, t, J=6.9 Hz), 2.90 (2H, t, J=6.9 Hz), 3.47 (3H, s), 5.03 (2H, s), 5.17 (2H, s), 6.56 (1H, dd, J=8.2, 2.5 Hz), 6.79 (1H, d, J=2.5 Hz), 7.04 (1H, d, J=8.2 Hz), 7.29-7.45 (5H, m)

(Step 6)

4-(2-Aminoethyl)-3-methoxymethoxyphenol

A mixture of 18.00 g of 2-(4-benzyloxy-2-methoxymethoxy phenyl)ethylamine, 3.6 g of 10% palladium on carbon (Degussa Inc.: E101 NE/W) and 230 mL of ethanol was stirred under a hydrogen atmosphere at room temperature for 1 hour. After the catalyst was filtered off through a diatomaceous earth, the filtrate was concentrated under reduced pressure to give 12.65 g of 4-(2-aminoethyl)-3-methoxymethoxyphenol as a colorless solid.

¹H-NMR (CD₃OD) δ ppm: 2.65-2.75 (2H, m), 2.75-2.85 (2H, m), 3.45 (3H, s), 5.16 (2H, s), 6.36 (1H, dd, J=8.1, 2.3 Hz), 6.58 (1H, d, J=2.3 Hz), 6.94 (1H, d, J=8.1 Hz)

(Step 7)

5-Carbamoyl-2-methoxybenzenesulfonyl chloride

To 1733 g of chlorosulfonic acid was added in small portions 150 g of 4-methoxybenzamide under ice-cooling with stirring during 15 minutes, and the mixture was stirred at room temperature for 14 hours. After being stirred at 50° C. for additional 1.5 hours, the reaction mixture was dropped into 7 kg of ice. The precipitate was collected by filtration, washed with water and hexane to give 230 g of 5-carbamoyl-2-methoxybenzenesulfonyl chloride.

¹H-NMR (DMSO-d₆) δ ppm: 3.81 (3H, s), 7.00 (1H, d, J=8.5 Hz), 7.10 (1H, br s), 7.84 (1H, dd, J=8.5, 2.5 Hz), 7.87 (1H, br s), 8.23 (1H, d, J=2.5 Hz)

(Step 8)

5-Cyano-2-methoxybenzenesulfonyl chloride

5-Carbamoyl-2-methoxybenzenesulfonyl chloride (150 g) was suspended in 1800 mL of ethyl acetate. After 219 mL of thionyl chloride was dropped to the stirred suspension under ice-cooling, 2.3 mL of N,N-dimethylformamide was added to the mixture. After being stirred at 55° C. for 3 hours, the reaction mixture was concentrated under reduced pressure. To the residue were added ethyl acetate and water, and the separated organic layer was washed with water, saturated aqueous sodium bicarbonate solution, and brine, and dried over anhydrous magnesium sulfate. The solvent was removed under reduced pressure, and the obtained crude product was recrystallized from ethyl acetate-hexane to give 86.8 g of 5-cyano-2-methoxybenzenesulfonyl chloride.

¹H-NMR (CDCl₃) δ ppm: 4.16 (3H, s), 7.24 (1H, d, J=8.8 Hz), 7.96 (1H, dd, J=8.8, 2.2 Hz), 8.28 (1H, d, J=2.2 Hz)

(Step 9)

5-Cyano-N-[2-(4-hydroxy-2-methoxymethoxyphenyl)ethyl]-2-methoxybenzenesulfonamide 4-(2-Aminoethyl)-3-methoxymethoxyphenol(12.3 g) and 7.9 g of sodium bicarbonate were suspended in a mixture of 133 mL of tetrahydrofuran and 14.4 mL of water. To the resulting suspension were added 18 mL portions of a solution of 14.50 g of 5-cyano-2-methoxybenzensulfonyl chloride in 180 mL of tetrahydrofuran every 10 minutes while the internal temperature was kept at 10-20° C. After being stirred at room temperature for 8 hours, the reaction mixture was purified by column chromatography on aminopropylated silica gel (eluent: ethyl acetate), and recrystallized from ethyl acetate-diisopropyl ether to give 21.87 g of 5-cyano-N-[2-(4-hydroxy-2-methoxy methoxyphenyl) ethyl]-2-methoxybenzenesulfonamide as a colorless crystal.

¹H-NMR (CDCl₃) δ ppm: 2.74 (2H, t, J=6.3 Hz), 3.10-3.20 (2H, m), 3.40 (3H, s), 3.81 (3H, s), 4.85-4.95 (2H, m), 5.08 (2H, s), 6.38 (1H, dd, J=8.2, 2.2 Hz), 6.59 (1H, d, J=2.2 Hz), 6.87 (1H, d, J=8.2 Hz), 7.00 (1H, d, J=8.5 Hz), 7.78 (1H, dd, J=8.5, 2.2 Hz), 8.16 (1H, d, J=2.2 Hz)

(Step 10)

4-[2-(5-Cyano-2-methoxybenzenesulfonylamino) ethyl]-3-methoxymethoxyphenyl trifluoromethanesulfonate To a stirred solution of 21.87 g of 5-cyano-N-[2-(4-hydroxy-2-methoxymethoxyphenyl)ethyl]-2-methoxybenzene sulfonamide and 10.21 g of N,N-dimethylaminopyridine in 230 mL of dichloromethane was added 9.38 mL of trifluoromethanesulfonic anhydride under ice-cooling. The mixture was stirred for 1 hour, and about 50 g of crushed ice was added to the reaction mixture. The mixture was concentrated under reduced pressure to remove dichloromethane, and the residue was poured into a mixture of 500 mL of ethyl acetate and 200 mL of water. The organic layer was separated, washed with water, dried over anhydrous magnesium sulfate, and filtered. The filtrate was concentrated under reduced pressure, and the residue was recrystallized from ethyl acetate-diisopropyl ether to give 24.75 g of 4-[2-(5-cyano-2-methoxybenzenesulfonylamino)ethyl]-3-methoxymethoxyphenyl trifluoromethanesulfonate as a colorless powder.

$^1$H-NMR (CDCl$_3$) δ ppm: 2.86 (2H, t, J=6.6 Hz), 3.15-3.25 (2H, m), 3.44 (3H, s), 3.86 (3H, s), 4.89 (1H, t, 3=6.0 Hz), 5.16 (2H, s), 6.86 (1H, dd, J=8.5, 2.2 Hz), 7.00-7.05 (2H, m), 7.12 (1H, d, J=8.5 Hz), 7.81 (1H, dd, J=8.5, 2.2 Hz), 8.20 (1H, d, J=2.2 Hz)

(Step 11)

5-Cyano-2-methoxy-N-[2-(3-methoxymethoxy-2'-methylthio-biphenyl-4-yl)ethyl]benzenesulfonamide A mixture of 24.75 g of 4-[2-(5-cyano-2-methoxybenzene sulfonylamino)ethyl]-3-methoxymethoxyphenyl trifluormethane sulfonate, 8.32 g of 2-(methylthio)phenylboronic acid, 2.73 g of tetrakis(triphenylphosphine)palladium(0), 728 mg of tetra-n-butylammonium bromide, 10.00 g of sodium carbonte, 48 mL of water and 285 mL of toluene was heated under an argon atmosphere at 85° C. for 15 hours. The precipitate was collected by filtration, washed successively with ethyl acetate and water to give 19.74 g of 5-cyano-2-methoxy-N-[2-(3-methoxymethoxy-2'-methylthiobiphenyl-4-yl)ethyl]benzenesulfonamide as an yellow powder.

$^1$H-NMR (CDCl$_3$) δ ppm: 2.40 (3H, s), 2.88 (2H, t, J=6.3 Hz), 3.19-3.27 (2H, m), 3.43 (3H, s), 3.82 (3H, s), 5.04 (1H, t, J=5.7 Hz), 5.17 (2H, s), 6.95-7.05 (2H, m), 7.08 (1H, d, J=7.6 Hz), 7.10-7.25 (3H, m), 7.25-7.30 (1H, m), 7.30-7.40 (1H, m), 7.79 (1H, dd, J=8.8, 2.2 Hz), 8.22 (1H, d, J=2.2 Hz)

(Step 12)

5-Cyano-N-[2-(2'-methanesulfonyl-3-methoxymethoxybiphenyl-4-yl)ethyl]-2-methoxybenzenesulfonamide To a stirred suspension of 26.44 g of 5-cyano-2-methoxy-N-[2-(3-methoxymethoxy-2'-methylthiobiphenyl-4-yl) ethyl] benzenesulfonamide and 35.6 g of sodium bicarbonate in a mixture of 530 mL of acetone and 106 mL of water was added two portions of 81.5 g of OXONE (trademark) every 15 minutes under ice-cooling. The mixture was stirred under the same condition for 3 hours, and 100 mL of diethyl ether, 100 mL of water, and saturated aqueous sodium sulfate solution were added to the stirred reaction mixture under ice-cooling. The resulting mixture was concentrated under reduced pressure to remove acetone, and thereafter 300 mL of water and diethyl ether-hexane were added to the stirred residue under ice-cooling. The mixture was stirred for 30 minutes, and the precipitate was collected by filtration, washed with water and diethyl ether-hexane to give 27.1 g of 5-cyano-N-[2-(2'-methanesulfonyl-3-methoxymethoxybiphenyl-4-yl)ethyl]-2-methoxybenzenesulfonamide as a white powder.

$^1$H-NMR (DMSO-d$_6$) δ ppm: 2.65-2.75 (2H, m), 2.79 (3H, s), 3.05-3.15 (2H, m), 3.30-3.35 (3H, m), 4.00 (3H, s), 5.15 (2H, s), 6.94 (1H, dd, J=7.6, 1.6 Hz), 7.06 (1H, d, J=1.6 Hz), 7.16 (1H, d, J=7.6 Hz), 7.35-7.45 (2H, m), 7.66 (1H, td, J=7.6, 1.3 Hz), 7.70-7.80 (2H, m), 8.05-8.15 (3H, m)

(Step 13)

5-Cyano-N-[2-(3-hydroxy-2'-methanesulfonylbiphenyl-4-yl) ethyl]-2-methoxybenzenesulfonamide To a suspension of 14.89 g of 5-cyano-N-[2-(2'-methanesulfonyl-3-methoxymethoxybiphenyl-4-yl)ethyl]-2-methoxybenzenesulfonamide in a mixture of 30 mL of isopropanol and 90 mL of tetrahydrofuran was added 11.7 mL of concentrated hydrochloric acid. After being stirred at 50° C. for 2 hours, the reaction mixture was diluted with 50 mL of water, and extracted with 150 mL of ethyl acetate. The organic layer was washed with saturated aqueous sodium bicarbonate solution, and brine, dried over anhydrous magnesium sulfate, and filtered. The filtrate was concentrated under reduced pressure, and the residue was purified by column chromatography on aminopropylated silica gel (eluent: ethyl acetate-methanol) to give 10.22 g of 5-cyano-N-[2-(3-hydroxy-2'-methanesulfonylbiphenyl-4-yl) ethyl]-2-methoxybenzenesulfonamide as a colorless amorphous.

$^1$H-NMR (CDCl$_3$) δ ppm: 2.69 (3H, s), 2.87 (2H, t, J=6.9 Hz), 3.20-3.30 (2H, m), 3.98 (3H, s), 5.34 (1H, t, J=5.7 Hz), 5.93 (1H, s), 6.88 (1H, dd, J=7.6, 1.6 Hz), 6.97 (1H, d, J=1.6 Hz), 7.05-7.15 (2H, m), 7.33 (1H, dd, J=7.6, 1.3H2), 7.56 (1H, td, J=7.6, 1.3 Hz), 7.65 (1H, td, J=7.6, 1.3 Hz), 7.82 (1H, dd, J=8.5, 2.2 Hz), 8.15-8.25 (2H, m)

(Step 14)

Ethyl[4-[2-(5-cyano-2-methoxybenzenesulfonylamino)ethyl]-2'-methanesulfonylbiphenyl-3-yloxy]acetate To a solution of 5.72 g of 5-cyano-N-[2-(3-hydroxy-2'-methanesulfonylbiphenyl-4-yl)ethyl]-2-methoxybenzene sulfonamide in 57 mL of N,N-dimethylformamide were added 2.46 mL of N,N-diisopropylethylamine and 1.37 mL of ethyl bromoacetate. After being stirred at 50° C. for 15 hours, the reaction mixture was poured into 100 mL of water, and extracted with a mixture of 150 mL of ethyl acetate and 20 mL of toluene. The organic layer was washed with water and brine, dried over anhydrous magnesium sulfate, and filtered. The filtrate was concentrated under reduced pressure, and the residue was purified by column chromatography on aminopropylated silica gel (eluent: ethyl acetate-hexane) to give 2.96 g of ethyl [4-[2-(5-cyano-2-methoxybenzenesulfonylamino)ethyl]-2'-methanesulfonyl biphenyl-3-yloxy]acetate as an amorphous.

$^1$H-NMR (CDCl$_3$) δ ppm: 1.28 (3H, t, J=6.9 Hz), 2.59 (3H, s), 2.95 (2H, t, J=6.6 Hz), 3.30-3.60 (2H, m), 3.99 (3H, s), 4.23 (2H, q, J=6.9 Hz), 4.68 (2H, s), 5.43 (1H, t, J=6.3 Hz), 6.95 (1H, dd, J=7.6, 1.6 Hz), 7.04 (1H, d, J=1.6 Hz), 7.09 (1H, d, J=8.5 Hz), 7.20 (1H, d, J=7.6 Hz), 7.36 (1H, dd, J=7.6, 1.3 Hz), 7.57 (1H, td, J=7.6, 1.3 Hz), 7.65 (1H, td, J=7.6, 1.3 Hz), 7.80 (1H, dd, J=8.5, 2.2 Hz), 8.20-8.25 (2H, m)

(Step 15)

Ethyl[4-[2-(5-cyano-2-hydroxybenzenesulfonylamino)ethyl]-2'-methanesulfonylbiphenyl-3-yloxy]acetate To a solution of 4.62 g of ethyl[4-[2-(5-cyano-2-methoxybenzenesulfonylamino)ethyl]-2'-methanesulfonyl biphenyl-3-yloxy]acetate in 40 mL of N,N-dimethylformamide was added 1.03 g of lithium chloride, and the mixture was stirred at 140° C. for 2 hours. After being cooled to room temperature, the reaction mixture was poured into a mixture of 60 mL of ethyl acetate, 6 mL of toluene, and 32 mL of 1 mol/L hydrochloric acid. The organic layer was separated, and washed with 1 mol/L hydrochloric acid and brine. The organic layer was dried over anhydrous magnesium sulfate, and filtered. The filtrate was concentrated under reduced pressure, and the residue was purified by column chromatography on aminopropylated silica gel (eluent: acetic acid-ethyl acetate) to give 3.67 g of ethyl [4-[2-(5-cyano-2-hydroxybenzenesulfonylamino)ethyl]-2'-methanesulfonylbiphenyl-3-yloxy]acetate as a colorless amorphous.

$^1$H-NMR (DMSO-d$_6$) δ ppm: 1.14 (3H, t, J=7.3 Hz), 2.71 (3H, s), 2.75-2.82 (2H, m), 3.07-3.16 (2H, m), 4.10 (2H, q, J=7.3 Hz), 4.75 (2H, s), 6.90-6.95 (2H, m), 7.12 (1H, d, J=8.5 Hz), 7.20-7.30 (1H, m), 7.38 (1H, dd, J=7.6, 1.3 Hz), 7.45-7.60 (1H, br s), 7.65 (1H, td, J=7.6, 1.3 Hz), 7.75 (1H, td, J=7.6, 1.3 Hz), 7.87 (1H, dd, J=8.5, 2.2 Hz), 8.01 (1H, d, J=2.2 Hz), 8.07 (1H, dd, J=7.6, 1.3 Hz), 11.80-12.30 (1H, br)

(Step 16)

Ethyl[4-[2-[2-hydroxy-5-(N-hydroxycarbamimidoyl) benzene sulfonylamino]ethyl]-2'-methanesulfonylbiphenyl-3-yloxy]acetate A suspension of 2.01 g of ethyl[4-[2-(5-cyano-2-hydroxy benzenesulfonylamino)ethyl-2'-methanesulfonylbiphenyl-3-yl oxy]acetate in 1.0 mL of saturated hydrogen chloride/ethanol solution was stirred at room temperature for 3 hours. The reaction mixture was concentrated under reduced pressure, and the residue was dissolved in 20.0 mL of ethanol. To this solution was added 3.34 g of hydroxylammonium acetate, and the mixture was stirred at room temperature for 13 hours. The reaction mixture was poured into ethyl acetate-water, and the organic layer was separated. After the aqueous layer was extracted with ethyl acetate, the organic layers were combined, and washed with brine. The organic layer was dried over anhydrous magnesium sulfate, and filtered. The filtrate was concentrated under reduced pressure, and the residue was purified by column chromatography on silica gel (eluent: ethyl acetate) to give 1.90 g of ethyl [4-[2-[2-hydroxy-5-(N-hydroxycarbamimidoyl)benzenesulfonyl amino]ethyl]-2'-methanesulfonylbiphenyl-3-yloxy] acetate as an amorphous.

$^1$H-NMR (DMSO-d$_6$) δ ppm: 1.12 (3H, t, J=6.9 Hz), 2.70 (3H, s), 2.75-2.85 (2, m), 3.00-3.10 (2H, m), 4.08 (2H, q, J=6.9 Hz), 4.75 (2H, s), 5.77 (2H, br s), 6.85-6.95 (2H, m), 6.97 (1H, d, J=8.5 Hz), 7.10-7.25 (2H, m), 7.35-7.40 (1H, m) 7.60-7.80 (3H, m), 7.95-8.10 (2H, m), 9.53 (1H, br s), 10.9 (1H, br s)

(Step 17)

Figure 3:
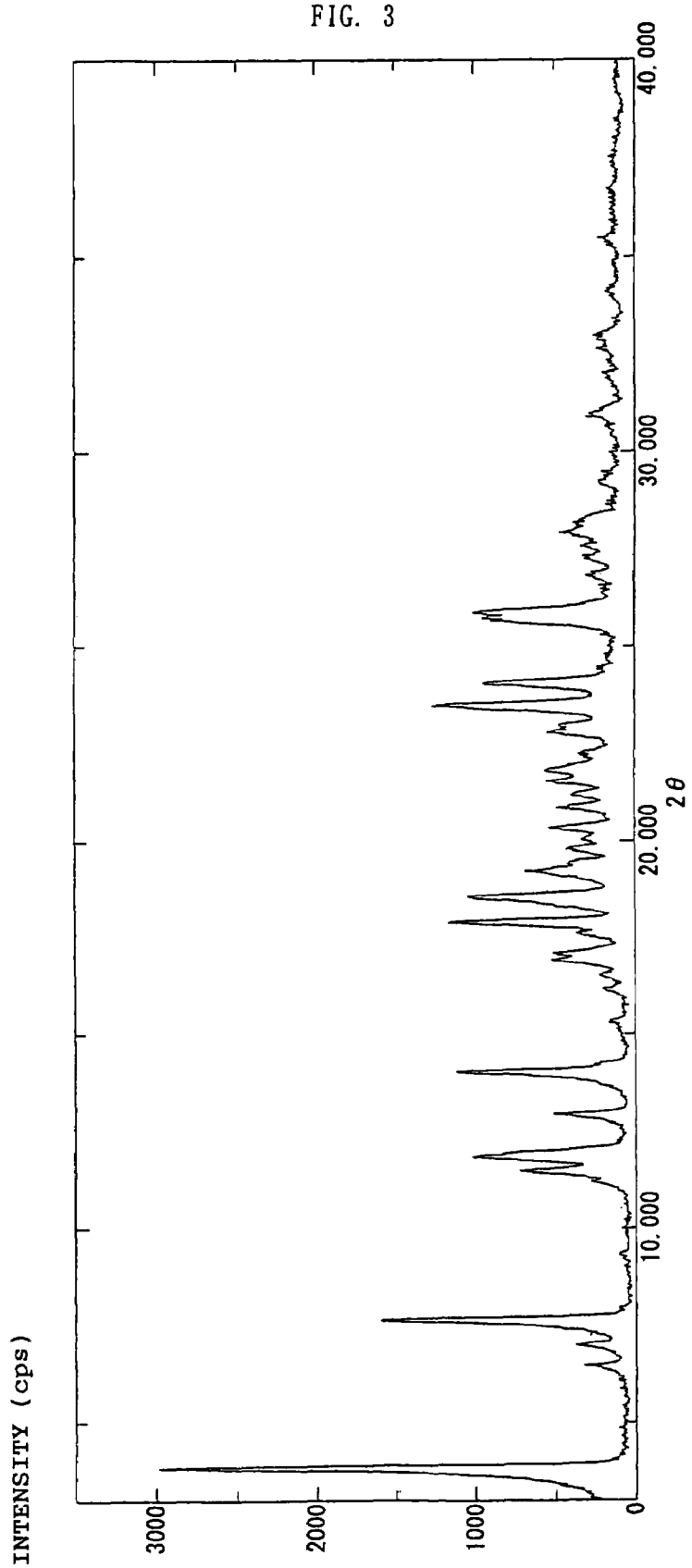
FIG. 3 is an X-ray powder diffraction pattern of crystalline form A of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride obtained in reference example 1 where the ordinate shows the X-ray intensity in cps and the abscissa shows the diffraction angle in 2θ.

Crystalline form A of n-butyl[4-[2-[2-hydroxy-5-(N-hydroxy carbamimidoyl)benzenesulfonylamino] ethyl]-2'-methane-sulfonylbiphenyl-3-yloxy]acetate hydrochloride A solution of 1.499 g of ethyl[4-[2-[2-hydroxy-5-(N-hydroxycarbamimidoyl)benzenesulfonylamino]ethyl]-2'-methane sulfonylbiphenyl-3-yloxy]acetate in 20 mL of 34% hydrogen chloride/n-butanol solution was stirred at 60° C. for 3 hours. The reaction mixture was concentrated under a reduced pressure, and the crude crystals were recrystallized from n-butanol/diisopropyl ether to give 1.472 g of n-butyl [4-[2-[2-hydroxy-5-(N-hydroxycarbamimidoyl)benzenesulfonyl amino]ethyl]-2'-methanesulfonylbiphenyl-3-yloxy] acetate hydrochloride as a white crystal. The crystals thus obtained were identified as crystalline form A by an X-ray powder diffraction analysis. An X-ray powder diffraction pattern of the crystals was shown in FIG. 3.

Melting point: 155° C.

$^1$H-NMR (DMSO-d$_6$) δ ppm: 0.78 (3H, t, J=7.6 Hz), 1.15-1.30 (2H, m), 1.40-1.55 (2H, m), 2.72 (3H, s), 2.75-2.85 (2H, m), 3.05-3.15 (2H, m), 4.05 (2H, t, J=6.6 Hz), 4.78 (2H, s), 6.90-6.95 (2H, m), 7.18 (1H, d, J=7.6 Hz), 7.20-7.30 (1H, m), 7.37 (1H, d, J=7.6 Hz), 7.42-7.50 (1H, m), 7.66 (1H, td, J=7.6, 1.3 Hz), 7.72-7.82 (2H, m), 8.02-8.10 (2H, m), 8.60-9.60 (1H, br), 10.85-11.30 (1H, br), 11.80-12.20 (1H, br), 12.50-13.05 (1H, br)

Reference Example 2

Figure 2:
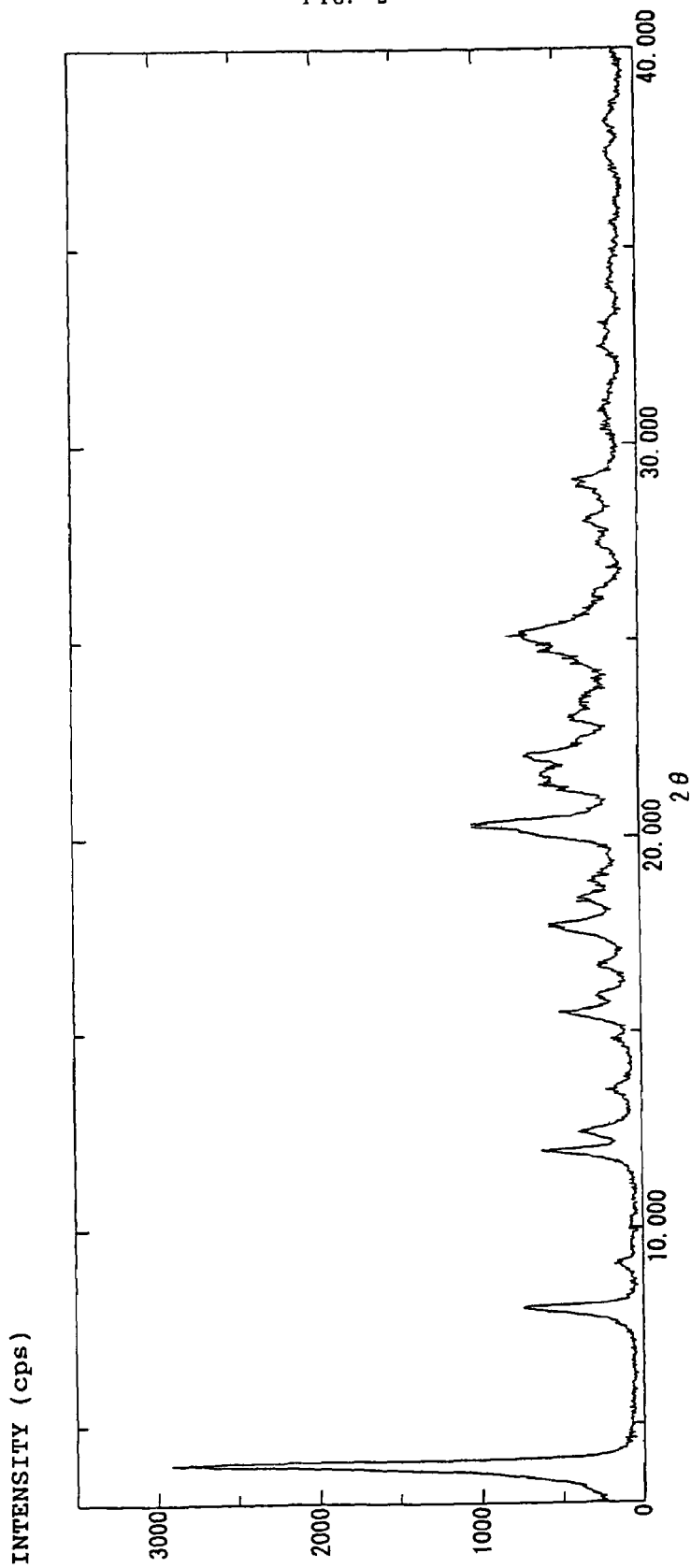
FIG. 2 is an X-ray powder diffraction pattern of a crystalline monohydrate of n-butyl[4-[2-[2-hydroxy-5-(N-hydroxycarbamimidoyl)benzenesulfonylamino]ethyl]-2'-methanesulfonylbiphenyl)-3-yloxy]acetate hydrochloride obtained in Reference example 2 where the ordinate shows the X-ray intensity in cps and the abscissa shows the diffraction angle in 2θ.

Crystals of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride monohydrate A mixture of the crude crystals of n-butyl [4-[2-[2-hydroxy-5-(N-hydroxycarbamimidoyl)benzenesulfonyl amino]ethyl]-2'-methanesulfonylbiphenyl-3-yloxy]acetate hydrochloride (827 mg) obtained in reference example 1 and 12.6 mL of 1 N hydrochloric acid was heated at 40° C. with stirring overnight. The resulting crystals were collected by filtration and dried at 40° C. under a reduced pressure overnight to give 823 mg of crystals. The crystals thus obtained were identified as n-butyl[4-[2-[2-hydroxy-5-(N-hydroxycarbamimidoyl) benzenesulfonylamino]ethyl]-2'-methanesulfonylbiphenyl-3-yl oxy]acetate hydrochloride monohydrate by a Karl Fischer water measurement. An X-ray powder diffraction pattern of the crystals was shown in FIG. 2.

Melting point: 133° C.

Example 1

Crystalline form B of n-butyl[4-[2-[2-hydroxy-5-(N-hydroxy carbamimidoyl)benzenesulfonylamino] ethyl]-2'-methanesulfonylbiphenyl-3-yloxy]acetate hydrochloride A mixture of the crude crystals of n-butyl [4-[2-[2-hydroxy-5-(N-hydroxycarbamimidoyl)benzenesulfonyl amino]ethyl]-2'-methanesulfonylbiphenyl-3-yloxy]acetate hydrochloride (476 g) obtained in reference example 1 and 2.1 Kg of n-butanol was heated at 86° C. with stirring until it appeared to be a clear solution. After insoluble materials were filtered off, the filtrate was cooled to 45° C., and 2.5 kg of ethyl acetate was added dropwise thereto at the same temperature. Then seed crystals of crystalline form B were added, and the resulting mixture was stirred at room temperature overnight for crystallization. The suspension was stirred under ice cooling for 5.5 hours, and the precipitated crystals were collected by filtration. The crystals were washed successively with ethyl acetate (150 g)/n-butanol (300 g) and ethyl acetate (650 g), dried under a reduced pressure at 40° C. overnight to give 360 g of crystals The crystals thus obtained were identified as crystalline form B by an X-ray powder diffraction analysis. An X-ray powder diffraction pattern of the crystals was shown in FIG. 1.

Melting point: 168° C.

Example 2

Crystalline form B of n-butyl[4-[2-[2-hydroxy-5-(N-hydroxy carbamimidoyl)benzenesulfonylamino]ethyl]-2'-methanesulfonylbiphenyl-3-yloxy]acetate hydrochloride A mixture of the crude crystals of n-butyl [4-[2-[2-hydroxy-5-(N-hydroxycarbamimidoyl)benzenesulfonyl amino]ethyl]-2'-methanesulfonylbiphenyl-3-yloxy]acetate hydrochloride (200 mg) obtained in reference example 1 and 1.2 mL of n-butanol was heated at 100° C. with stirring until it appeared to be a clear solution. The solution was cooled to room temperature, and 1.2 mL of methyl ethyl ketone was added thereto. The resulting mixture was stirred at room temperature overnight for crystallization. The precipitated crystals were collected by filtration, washed with 0.8 mL of ethyl acetate, and dried under a reduced pressure at 40° C. overnight to give 135 mg of crystals. The crystals thus obtained were identified as crystalline form B by an X-ray powder diffraction analysis.

Melting point: 168° C.

Example 3

Crystalline form B of n-butyl[4-[2-[2-hydroxy-5-(N-hydroxycarbamimidoyl)benzenesulfonylamino]ethyl]-2'-methane sulfonylbiphenyl-3-yloxy]acetate hydrochloride A mixture of the crude crystals of n-butyl [4-[2-[2-hydroxy-5-(N-hydroxycarbamimidoyl)benzenesulfonyl amino]ethyl]-2'-methanesulfonylbiphenyl-3-yloxy]acetate hydrochloride (100 mg) obtained in reference example 1 and 1.0 mL of n-butanol was heated at 90° C. with stirring until it appeared to be a clear solution. The mixture was cooled to room temperature, and 0.8 mL of 1,2-dimethoxyethane was added dropwise thereto. The resulting mixture was stirred at room temperature overnight for crystallization. The precipitated crystals were collected by filtration, washed with 0.8 mL of ethyl acetate, and dried under a reduced pressure at 40° C. overnight to give 52 mg of crystals. The crystals thus obtained were identified as crystalline form B by an X-ray powder diffraction analysis.

Melting point: 168° C.

Test Example 1

(Storage Stability Test)

Stability test was carried out under a storage condition of 40° C./90% relative humidity for two months for test substances. The residual rates of test substances were determined by HPLC according to the following conditions. The results were shown in table 1.

HPLC Condition:
  Detection wavelength; 225 nm
  Column; CAPCELL PAK C18, MG 5 μm, 3.0 mm I.D.× 250 mm
  Column temperature; 35° C.
  Mobile phase;
    0.02 mol/L phosphate buffer (pH 6.0): acetonitrile mixed solvent
    0→20 min; 42:58
    20→40 min; 42:58→70:30
    40→45 min; 70:30
  Flow rate; 0.5 mL/min

TABLE 1

| Test Substance | Residual Rate (%) |
| --- | --- |
| Reference Example 1 | 96.8 |
| Example 1 | 99.0 |

Test Example 2

(Saturated Water Solubility)

Approximately 40 mg of test substances is placed in a vessel, and approximately 15 mL of water is added thereto to suspend. The suspensions are warmed at 37° C. with stirring, and approximately 1 mL of aliquots is collected with time. Each of aliquots is filtered through a 0.45 μm filter. Thereafter, 500 μL is taken accurately from the filtrate, and 500 μL of a mixed solvent of water/acetonitrile (1/1) is added thereto to prepare a test solution. Five μL of the test solution is analyzed by a high performance liquid chromatography method according to the following conditions. Among water solubilities at each point of test solutions, the highest concentration is estimated as a saturated water solubility. The results were shown in table 2.

HPLC Condition:
  Detection wavelength; 225 nm
  Column; Inertsil ODS-3, 5 μm, 4.6 mm I.D.×250 mm
  Column temperature; 30° C.
  Mobile phase;
    0.02 mol/L phosphate buffer (pH 3.0): acetonitrile mixed solvent
    0→30 min; 42:58
  Flow rate; 11.0 mL/min
  Measurement time; 30 min

TABLE 2

| Test Substance | Saturated water solubility (μg/mL) |
| --- | --- |
| Reference Example 2 | 270 |
| Example 1 | 1600 |

Test Example 3

(Measurement of Activated Blood Coagulation Factor X Inhibitory Activity and Prothrombin Time (PT))

Male Wistar rats aged 6-9 weeks (SLC) fasted overnight were used. Test substances were suspended in 0.5% methylcellulose solution at the concentration of 6.0 mg/mL. Then 5.0 mL/kg of those was orally administrated into the rats. Then, 30 minutes before and after the administration of the test substances, citrated (1:10 dilution, 3.13% sodium citrate) bloods were collected from the jugular vein. Plasma samples were obtained by centrifugation. Effects of test substances on activated blood coagulation factor X and prothrombin time (PT) were investigated using the plasma samples according to the following procedures.

1) Activated Blood Coagulation Factor X Inhibitory Activity 2.5 μL of plasma sample, 200 μL of 100 mM tris-200 mM NaCl buffer (pH 8.4) and 10 μL of 0.06 U/mL human activated blood coagulation factor X (Calbiochem) in gelatin-glycine buffer were poured into 96 well microplate. Then 50 μL of 1 mM S-2222 (Daiichi Pure Chemicals) aqueous solution was added and the mixture was incubated for 10 minutes at room temperature. The reaction was terminated with the addition of 50 μL of 60% acetic acid and absorbance (405 nm) was measured by a microplate reader (SPECTRAmax250, Molecular Devices). The group with 2.5 μL of the control plasma instead of the plasma sample was defined as the control, and the group with 10 μL of gelatin-glycine buffer solution instead of human activated blood coagulation factor X was defined as the blank. The inhibitory % of plasma sample was calculated from absorbance of the control as 100% and this value was used as the index of anti-activated blood coagulation factor X activity in plasma. The result was shown in table 3.

2) Prothrombin Time (PT).

Fifty μL of plasma was put in the process tube and then incubated at 37° C. One minute later, 100 mu L of plasma PT reagent (Boehringer Mannheim) prewarmed at 37° C. was added into the mixture. PT was measured with a coagulometer (ST4, Boehringer Mannheim). The ratio of PT at each time point after administration of the test substance to that of before administration was used as the index of anticoagulation activity. The result was shown in table 3.

TABLE 3

| Test Substance | Activated blood coagulation factor X inhibitory activity (%) | Ratio of PT |
|---|---|---|
| Example 1 | 58.2 | 1.50 |

INDUSTRIAL APPLICABILITY

Crystalline form B of n-butyl[4-[2-[2-hydroxy-5-(N-hydroxycarbamimidoyl)benzenesulfonylamino]ethyl]-2'-methane sulfonylbiphenyl-3-yloxy]acetate hydrochloride of the present invention has a high filtration rate and good handling properties. Crystalline form B of the present invention can be obtained in high purity by a convenient purification procedure, and is suitable for a commercial production. Furthermore, crystalline form B of the present invention is highly water-soluble and has a good oral bioavailability. Crystalline form B of the present invention has good storage stabilities, and are suitable for pharmaceutical formulations. Therefore, crystalline form B of the present invention is useful as a drug substance.

The invention claimed is:

1. A crystal of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride, which shows an X-ray powder diffraction pattern having characteristic peaks at a diffraction angle (2θ±0.1 degree) of 5.4, 8.6, 9.1, 12.1, 16.7, 17.3 and 21.0 degrees.

2. A method for treating a thromboembolic disease, which comprises administering a therapeutically effective amount of a crystal according to claim 1.

* * * * *